United States Patent
Melapudi et al.

(10) Patent No.: US 11,657,501 B2
(45) Date of Patent: May 23, 2023

(54) GENERATING ENHANCED X-RAY IMAGES USING CONSTITUENT IMAGE

(71) Applicant: GE Precision Healthcare LLC, Milwaukee, WI (US)

(72) Inventors: Vikram Melapudi, Bengaluru (IN); Bipul Das, Chennai (IN); Krishna Seetharam Shriram, Bengaluru (IN); Prasad Sudhakar, Bengaluru (IN); Rakesh Mullick, Bengaluru (IN); Sohan Rashmi Ranjan, Bengaluru (IN); Utkarsh Agarwal, Bengaluru (IN)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 155 days.

(21) Appl. No.: 17/122,709

(22) Filed: Dec. 15, 2020

(65) Prior Publication Data

US 2022/0092768 A1 Mar. 24, 2022

(30) Foreign Application Priority Data

Sep. 24, 2020 (IN) .............................. 202041041437

(51) Int. Cl.
| | |
|---|---|
| G06T 7/00 | (2017.01) |
| G06T 5/00 | (2006.01) |
| G06T 7/10 | (2017.01) |
| G06T 11/00 | (2006.01) |
| A61B 6/00 | (2006.01) |

(52) U.S. Cl.
CPC ............ *G06T 7/0012* (2013.01); *A61B 6/482* (2013.01); *G06T 5/00* (2013.01); *G06T 7/10* (2017.01);

(Continued)

(58) Field of Classification Search
CPC ........... G06T 7/0012; G06T 5/00; G06T 7/10; G06T 11/003; G06T 2207/10081;

(Continued)

(56) References Cited

U.S. PATENT DOCUMENTS

| | | | |
|---|---|---|---|
| 2019/0122075 A1* | 4/2019 | Zhang | G16H 50/50 |
| 2020/0311912 A1* | 10/2020 | Knoplioch | G06T 7/11 |
| 2021/0248716 A1* | 8/2021 | Vera-Gonzalez | G06T 7/174 |

OTHER PUBLICATIONS

Albarqouni et al., "X-ray In-Depth Decomposition: Revealing The Latent Structures," arXiv:1612.06096v2 [cs.CV]; Mar. 22, 2017; 8 pages.

(Continued)

*Primary Examiner* — Siamak Harandi
(74) *Attorney, Agent, or Firm* — Amin, Turocy & Watson, LLP

(57) ABSTRACT

Techniques are provided for generating enhanced image representations from original X-ray images using deep learning techniques. In one embodiment, a system is provided that includes a memory storing computer executable components and a processor that executes the computer executable components stored in the memory. The computer executable components can include a reception component, an analysis component, and an artificial intelligence component. The analysis component analyzes the original X-ray image using an AI-based model with respect to a set of features of interest. The AI component generates a plurality of enhanced image representations. Each enhanced image representation highlights a subset of the features of interest and suppresses remaining features of interest in the set that are external to the subset.

20 Claims, 9 Drawing Sheets

(52) U.S. Cl.
CPC .. *G06T 11/003* (2013.01); *G06T 2207/10081* (2013.01); *G06T 2207/10088* (2013.01); *G06T 2207/10104* (2013.01); *G06T 2207/10116* (2013.01); *G06T 2207/20081* (2013.01)

(58) Field of Classification Search
CPC . G06T 2207/10088; G06T 2207/10104; G06T 2207/10116; G06T 2207/20081; G06T 5/008; G06T 11/008; A61B 6/482; A61B 6/5217; G06V 2201/03; G06V 10/82
See application file for complete search history.

(56) References Cited

OTHER PUBLICATIONS

Li et al., "Encoding CT Anatomy Knowledge for Unpaired Chest X-ray Image Decomposition," arXiv:1909.12922v1 [eess.IV]; Sep. 16, 2019; 9 pages.

Moturu et al., "Creation of Synthetic X-Rays to Train a Neural Network to Detect Lung Cancer," Department of Computer Science, University of Toronto, Toronto, Ontario, Canada, Aug. 20, 2018, 16 pages.

EP application 21196433.3 filed Sep. 13, 2021—extended Search Report dated Mar. 14, 2022; 11 pages.

Li Han et al.: "High-Resolution Chest X-Ray Bone Suppression Using Unpaired CT Structural Priors", IEEE Transactions On Medical Imaging, IEEE, USA, vol. 39, No. 10, Apr. 6, 2020 (Apr. 6, 2020), pp. 3053-3063, XP011811576, ISSN: 0278-0062, DOI: 10.1109/TMI.2020.2986242 [retrieved on Sep. 30, 2020].

Ophir Gozes et al: "Lung Structures Enhancement in Chest Radiographs via CT based FCNN Training", arxiv.org, Cornell University Library, 201 OLIN Library Cornell University Ithaca, NY 14853, Oct. 14, 2018 (Oct. 14, 2018), XP081065454, DOI: 10.1007/978-3-030-00946-5_16.

* cited by examiner

GENERATING ENHANCED X-RAY IMAGES USING CONSTITUENT IMAGE

TECHNICAL FIELD

This application generally relates to deep learning techniques and more particularly to computer-implemented techniques for generating enhanced image representations using deep learning techniques.

BACKGROUND

X-ray imaging is a medical imaging modality that is widely employed for first-line diagnosis and continuous evaluation. In some instances, X-ray imaging is also employed for both detection and daily diagnosis of disease progression. X-ray imaging is a projection-based imaging modality in which each image pixel depicts a summation of information along a given projection depth. In essence, X-ray images are two-dimensional projections of three-dimensional maps in which some available information is obscured by virtue of summative effects. For example, bone tissue offers higher attenuation to X-rays during imaging, and thus the bone tissue will mask tissue variations in the same projection path corresponding to tissues that off lower attenuation to X-rays.

On occasion, it may be beneficial to provide medical images depicting particular features of interest that are unobstructed by other features of interest. For example, early symptoms of the coronavirus disease, COVID-19, manifest as ground glass opacities (GGOs) in lung tissue. Yet, the lower lobes of lung tissue where such GGOs may manifest are generally obscured by liver tissue or cardiac tissue in X-ray images. Computed tomography (CT) imaging may be useful in obtaining unobstructed views of the lower lobes of lung tissue. However, CT imaging is typically more expensive and time consuming than X-ray imaging. Furthermore, patients receive higher dosages of radiation from CT imaging than would be received from X-ray imaging.

SUMMARY

The following presents a summary to provide a basic understanding of one or more embodiments of the invention. This summary is not intended to identify key or critical elements or to delineate any scope of the particular embodiments or any scope of the claims. Its sole purpose is to present concepts in a simplified form as a prelude to the more detailed description that is presented later. In one or more embodiments described herein, systems, computer-implemented methods, apparatus and/or computer program products that facilitate generating enhanced image representations using deep learning techniques.

According to an embodiment, a system is provided that includes a memory storing computer executable components and a processor that executes the computer executable components stored in the memory. The computer executable components can include a reception component, an analysis component, and an artificial intelligence (AI) component. The reception component receives an original X-ray image. The analysis component analyzes the original X-ray image using an AI based model with respect to a set of features of interest. The AI component generates a plurality of enhanced image representations. Each enhanced image representation highlights a subset of the features of interest and suppresses remaining features of interest in the set that are external to the subset.

In some embodiments, the computer executable components can further include a training component that employs machine learning to train the AI based model. In some embodiments, the training component utilizes computer tomography (CT) volumes as training data. In some embodiments, the AI based model comprises a first AI subsystem that decomposes the original X-ray image into a set of constituent images and a second AI subsystem that combines a subset of the constituent images to generate a reconstructed X-ray image of the original X-ray image. In some embodiments, an error value is generated based on a comparison of the original X-ray image to the reconstructed X-ray image. In some embodiments, a confidence score associated with the plurality of enhanced image representations is generated based on the error value.

In some embodiments, the computer executable components can further include a rendering component that displays the original X-ray image and an enhanced image representation from the plurality of enhanced image representations. In some embodiments, the computer executable components can further include a selection component that provides for selecting particular features of interest to selectively mask or generate.

In some embodiments, elements described in connection with the disclosed computer-implemented methods can be embodied in different forms such as a computer system, a computer program product, or another form.

BRIEF DESCRIPTION OF THE DRAWINGS

Numerous aspects, implementations, objects and advantages of the present invention will be apparent upon consideration of the following detailed description, taken in conjunction with the accompanying drawings, in which like reference characters refer to like parts throughout, and in which.

DETAILED DESCRIPTION

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

Figure 1:
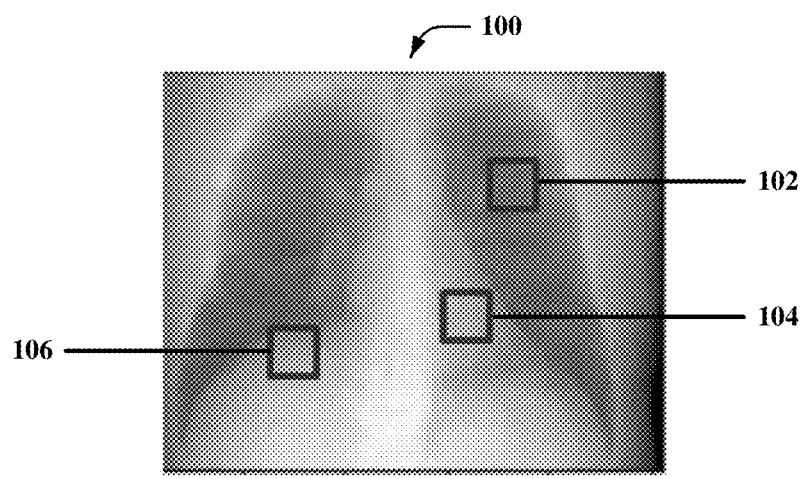
FIG. 1 illustrates an example original X-ray image depicting a human chest region, in accordance with one or more embodiments described herein.

The subject disclosure provides systems, computer-implemented methods, apparatus and/or computer program products that facilitate generating enhanced image representations from original X-ray images using deep learning techniques. Referring to FIG. 1, an example original X-ray image 100 is illustrated. Generally, radiography is a projection-based imaging modality in which a radiation source emits X-ray beams towards a radiation detector via a medium (e.g., a patient) being imaged. While propagating through the medium, a portion of the X-ray beam energy is absorbed by different materials composing the medium at varying rates depending on the density and composition of a given material.

The attenuated X-ray beam energy is detected by the radiation detector after passing through the medium. This detected energy produces signals that represent an intensity of X-ray beam energy incident on the radiation detector. Those signals are processed to generate projection data that includes line integrals of attenuation coefficients of the medium along propagation paths between the radiation source and the radiation detector. X-ray images (e.g., X-ray image 100) are formed from such projection data using various reconstruction techniques (e.g., filtered backpropagation). Through such reconstruction techniques, each pixel of an X-ray image is assigned a grayscale value that is proportional to an attenuation coefficient value associated with that pixel in the projection data.

One aspect of using projection data comprising line integrals of attenuation coefficients to generate X-ray images is that each pixel of a given X-ray image is a summation of information from multiple depths along an associated propagation path. Representing depth information for each propagation path in a summative manner introduces obstructive effects into X-ray images. For example, materials having higher attenuation coefficients (e.g., bone tissue) will obstruct or shadow other materials in a common propagation path that have lower attenuation coefficients (e.g., lung tissue) in an X-ray image. Such obstructive effects translate into subtle variations in intensity values within regions of an X-ray image that are associated with multiple materials having different attenuation coefficients.

By way of example, X-ray image 100 includes a number of image regions that illustrate such obstructive effects. In this example, image region 102 is associated with a propagation path that includes both bone tissue and lung tissue. Image region 104 is associated with a propagation path that includes bone tissue, lung tissue, and liver tissue. Image region 106 is associated with a propagation path that includes bone tissue, lung tissue, and cardiac tissue. As shown in FIG. 1, while multiple features of interest exist within each image region of X-ray image 100, visually distinguishing between individual features of interest may be challenging due to the obstructive effects discussed above. This is especially true in image regions where the variations in intensity values are particularly subtle, such as image region 106.

Figure 2:
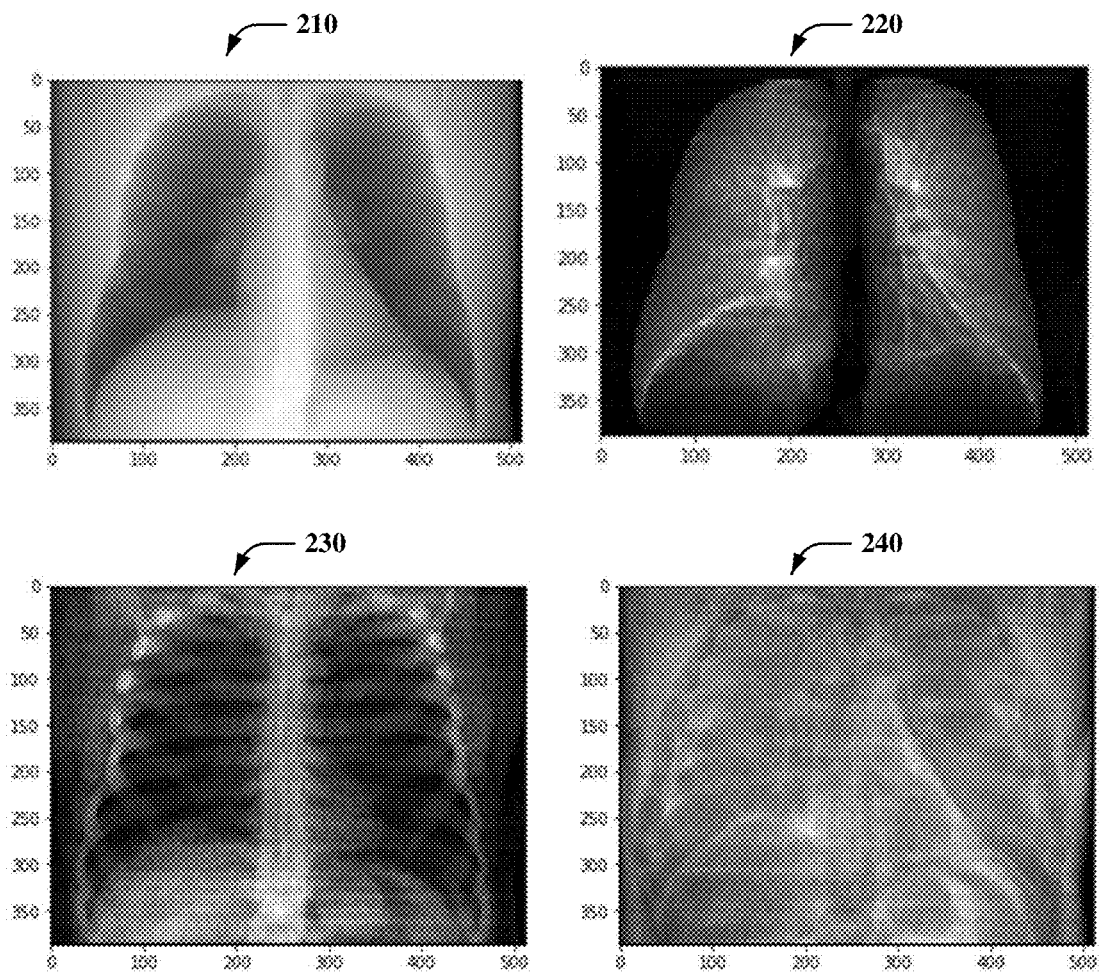
FIG. 2 illustrates example enhanced image representations generated using the original X-ray image illustrated in FIG. 1, in accordance with one or more embodiments described herein.

To mitigate such obstructive effects, the present disclosure leverages deep learning techniques to generate enhanced image representations using original X-ray images, as discussed in greater detail below. FIG. 2 illustrates example enhanced image representations that were generated using the original X-ray image illustrated in FIG. 1, in accordance with one or more embodiments described herein. As shown in FIG. 2, each enhanced image representation highlights, accentuates, or enhances different features of interest from X-ray image 100. For example, the feature of interest that enhanced image representation 210 highlights include multiple features of interest that correspond to various body tissue that is external to the lung tissue. Lung tissue is the feature of interest that enhanced image representation 220 highlights. In enhanced image representation 230, bone tissue is the feature of interest that is highlighted. Epithelial tissue is the feature of interest that enhanced image representation 240 highlights.

Figure 3:
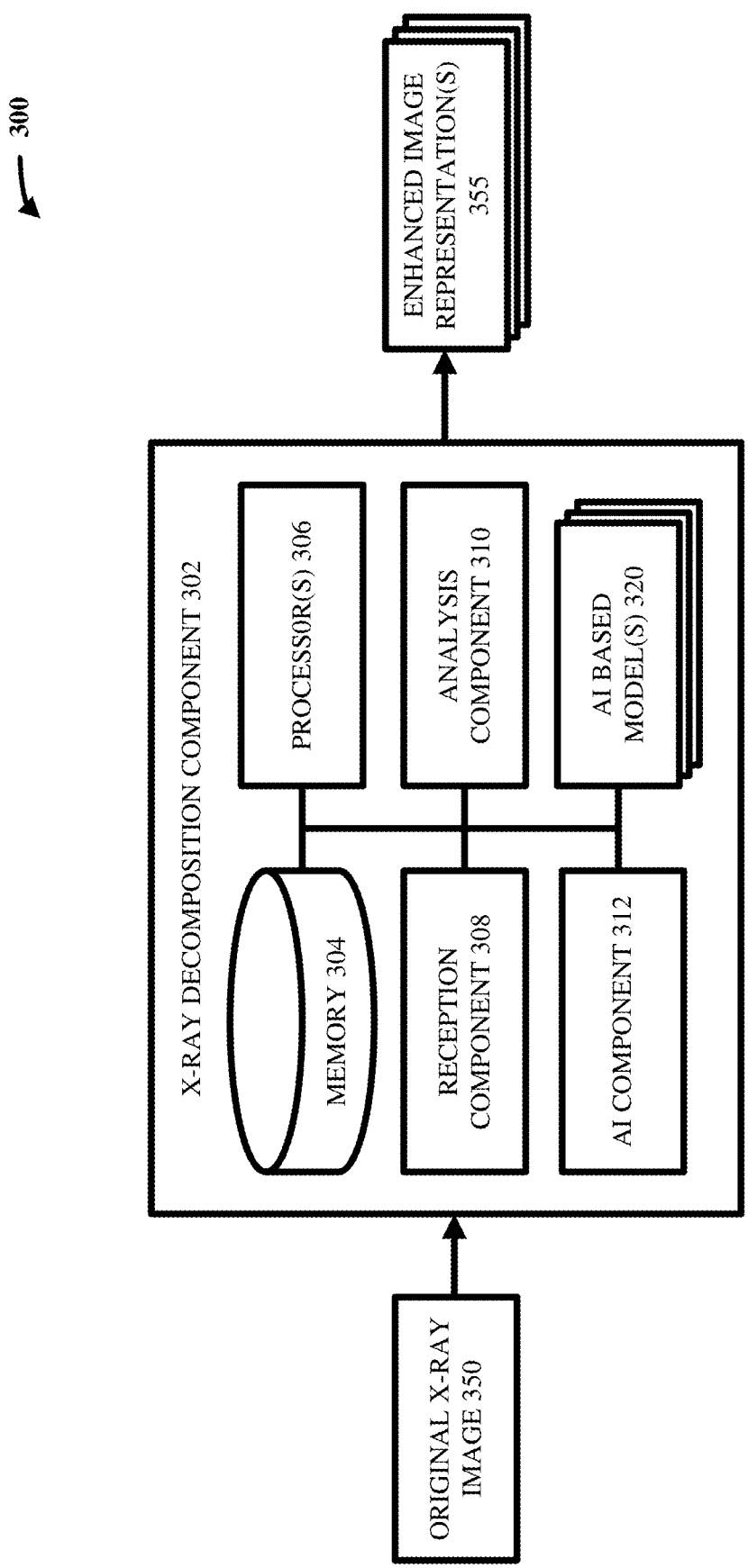
FIG. 3 illustrates a block diagram of an example system that facilitates generating enhanced image representations, in accordance with one or more embodiments described herein.

FIG. 3 illustrates a block diagram of an example system 300 that facilitates generating enhanced image representations, in accordance with one or more embodiments described herein. System 300 includes an X-ray decomposition component 302 that generates one or more enhanced image representations 355 from an original X-ray image 350. X-ray decomposition component 302 includes memory 304 for storing computer-executable components and one or more processors 306 operably coupled to memory 304 for executing the computer-executable components stored in memory 304. As shown in FIG. 3, the computer-executable components include: reception component 308; analysis component 310; and artificial intelligence (AI) component 312.

Reception component 308 can receive an original X-ray image 350 for use in generating one or more enhanced image representations. In an embodiment, reception component 308 receives the original X-ray image 350 directly from an imaging device (e.g., an X-ray scanner) that generates, captures, and/or creates the original X-ray image 350. In an embodiment, reception component 308 receives the original X-ray image 350 from a remote computing device via a network interface. In an embodiment, reception component 308 receives the original X-ray image 350 from a database or data structure that is accessible to X-ray decomposition component 302. In an embodiment, the database or data structure resides in memory 304. In an embodiment, the database or data structure is accessible to X-ray decomposition component 302 via a network interface.

Analysis component 310 can analyze the original X-ray image 350 with respect to a set of features of interest using an AI based model 320. In an embodiment, the AI based model 320 is implemented using network architecture 600, which is illustrated and described in greater detail below with respect to FIG. 6. In analyzing the original X-ray image 350, analysis component 310 can apply the AI based model 320 to identify a set of features of interest. By way of example, the set of features of interest can include bone tissue, epithelial tissue, lung tissue, and various body tissue that is external to the lung tissue, as discussed above with respect to FIG. 2. The type of deep learning architecture employed for the AI based model 320 can vary. In some embodiments, the AI based model 320 can employ a convolutional neural network (CNN) architecture. Other suitable deep learning architectures for the AI based model 320 can include but are not limited to, recurrent neural networks, recursive neural networks, and classical neural networks.

AI component 312 can generate a plurality of enhanced image representations using a set of constituent images obtained using the AI based model 320. Each enhanced image representation highlights a subset of the features of interest and suppresses remaining features of interest in the set that are external to the subset. In an embodiment, AI component 312 applies a filter that partitions the set of constituent images into multiple subsets of constituent images. In an embodiment, the multiple subsets of constituent images include a first subset of constituent images associated with the subset of the features of interest that a given enhanced image representation highlights. In an embodiment, the multiple subsets of constituent images include a second subset of constituent images associated with the remaining features of interest in the set that are external to the subset, which the given enhanced image representation suppresses. In an embodiment, AI component 312 enhances the subset of the features to generate the enhanced image representation by applying one or more image processing functions to the one or more constituent images associated with the subset of the features. Examples of suitable image processing functions include: edge enhancement, intensity rescaling, contrast enhancement, noise reduction, image smoothing, contrast stretching, gamma correction, and the like. In an embodiment, AI component 312 enhances the subset of the features to generate the enhanced image representations by applying an identity transformation to the one or more constituent images associated with the subset of the features.

Figure 4:
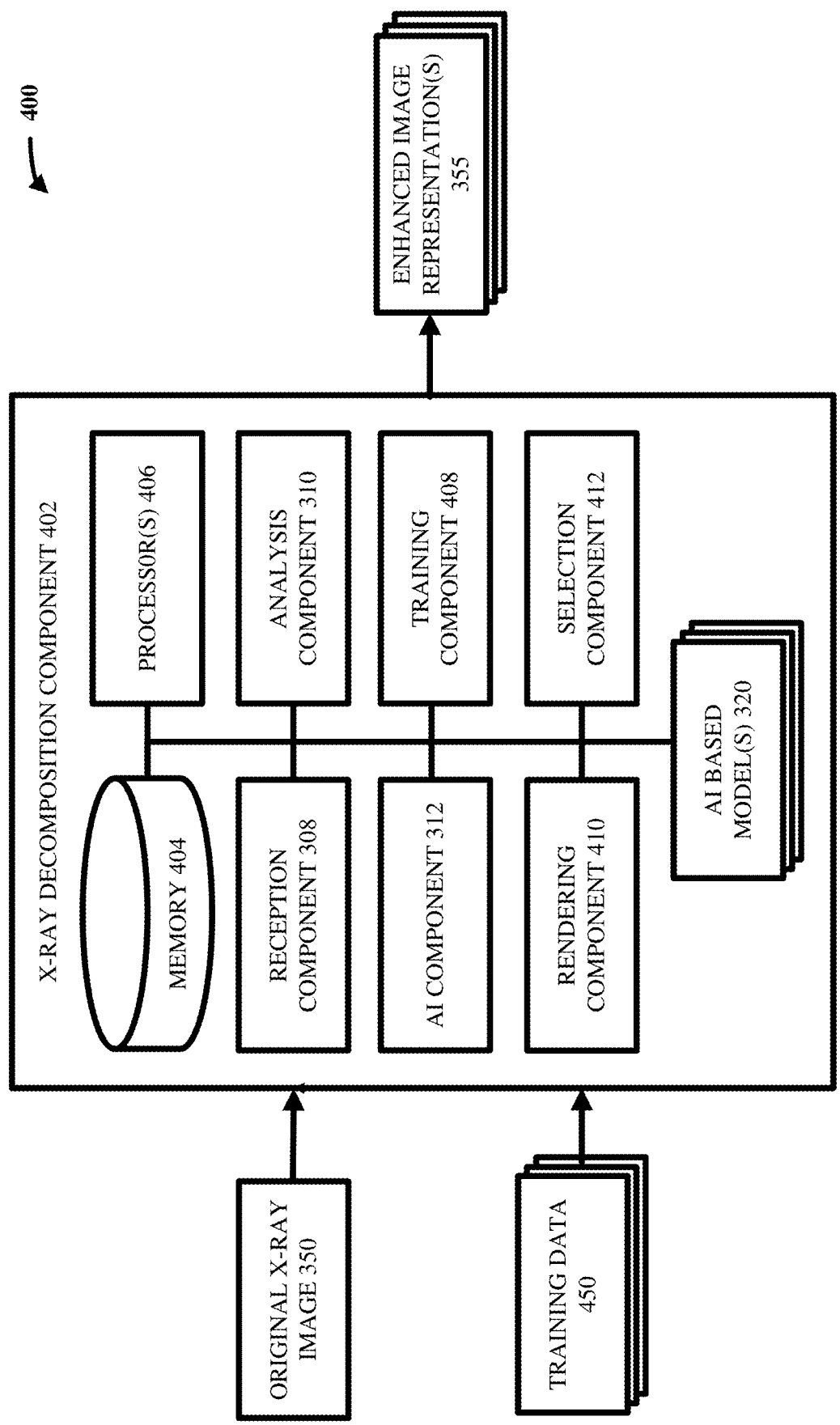
FIG. 4 illustrates a block diagram of another example system that facilitates generating enhanced image representations, in accordance with one or more embodiments described herein.

FIG. 4 illustrates a block diagram of another example system 400 that facilitates generating enhanced image representations, in accordance with one or more embodiments described herein. System 400 includes an X-ray decomposition component 402 that generates one or more enhanced image representations 355 from an original X-ray image 350. X-ray decomposition component 402 includes memory 404 for storing computer-executable components and one or more processors 406 operably coupled to memory 404 for executing the computer-executable components stored in memory 404. Similar to memory 304 of FIG. 3, the computer-executable components stored in memory 404 include: reception component 308; analysis component 310; and AI component 312. As seen in FIG. 4, the computer-executable components stored in memory 404 further include: training component 408; rendering component 410; and selection component 412.

Training component 408 can employ machine learning to train the AI based model 320. In training the AI based model 320, training component 408 retrieves multiple sets of training images from training data 450. Each set of training images includes an X-ray image generated from training data 450 and a set of corresponding ground truth (GT) constituent images generated from that X-ray image generated from training data 450. Training component 408 can generate such corresponding GT constituent images for training the AI based model 320, as illustrated and described below with respect to FIG. 5.

In an embodiment, training data 450 includes information derived from other imaging modalities (e.g., imaging modalities that were not used to generate, capture, and/or create original X-ray image 350). Examples of the other imaging modalities include: computed tomography (CT) volumes, magnetic resonance imaging (MRI) data, positron emission tomography (PET) data, and the like. In an embodiment, training data 450 includes information derived from different forms of a same imaging modality (e.g., different forms of the imaging modality that was used to generate, capture, and/or create original X-ray image 350), such as multi-energy X-ray imaging data. In an embodiment, training data 450 includes information derived from other imaging modalities, information derived from different forms of a same imaging modality, or a combination thereof.

Each corresponding GT constituent image is defined by a different constituent image definition that corresponds to one or more features of interest within the associated X-ray image. In an embodiment, each constituent definition associated with a given set of training images is configured such that a recombination of the set of GT constituent images reconstructs the corresponding X-ray image. Defining each corresponding GT constituent image with a different constituent image definition provides training component 408 with a mechanism that facilitates configuring the AI based model 320 for application specific decomposition.

For example, a particular application may involve presenting users of system 400 with an unobstructed view of lung tissue depicted in an X-ray image. As discussed above with respect to FIG. 1, some regions of lung tissue (e.g., region 106) depicted in an X-ray image may be obstructed by other materials having different attenuation coefficient values. Such regions of lung tissue can correspond to the lower lobes of lung tissue where ground glass opacities (GGOs) may be generally obscured by liver tissue or cardiac tissue in X-ray images. In this example, training component 408 may utilize a first constituent definition that corresponds to lung tissue and a second constituent definition that corresponds each remaining feature of interest external to lung tissue (e.g., bone tissue) within the X-ray image. Presenting users of system 400 with the unobstructed view of lung tissue using the first and second constituent definitions of this example can facilitate early COVID-19 symptom identification.

From each retrieved set of training images, training component 408 inputs an X-ray image into the AI based model 320. The AI based model 320 decomposes each X-ray image into a set of constituent images and generates a reconstructed X-ray image using the set of constituent images. In an embodiment, the AI based model 320 combines the set of constituent images to generate the reconstructed X-ray image. In an embodiment, the AI based model 320 combines a subset of the constituent images to generate the reconstructed X-ray image.

For each set of training images, training component 408 utilizes a loss function that operates on both a decomposed set of constituent images and a corresponding reconstructed X-ray image. Values that training component 408 obtains from the loss function are backpropagated to guide training of the AI based model 320. In an embodiment, the loss function may be implemented using the loss function defined by Equation 1:

$$\mathcal{L} = \sum_i \left\| X'_i - X'^{GT}_i \right\| + \mu \cdot \| X - X'' \| + \sum_i \rho_i \cdot \varphi_i(X'_i). \quad \text{Equation 1}$$

In accordance with Equation 1 above, $X'_i$ is the $i^{th}$ decomposed constituent image, $X'^{GT}_i$ is the ground truth image corresponding to the $i^{th}$ decomposed constituent image, $\mu$ is a scalar value that weights the reconstruction loss, $X$ is an original X-ray image, $X''$ is a reconstructed X-ray image generated using decomposed constituent images, $\rho_i$ is a scalar value that weights the $i^{th}$ regularization term, and $\varphi_i(\cdot)$ is a regularization function that operates on the $i^{th}$ decomposed constituent image and the corresponding ground truth constituent image. In an embodiment, the regularization function, $\varphi_i(\cdot)$, quantifies a similarity between an $i^{th}$ decomposed constituent image and corresponding ground truth constituent image using a structural similarity index metric (SSIM), a total variation loss metric, and the like.

The loss function of Equation 1 includes a data fidelity term that facilitates self-regularization of the decomposition process implemented by the AI based model 320. That data fidelity term is represented in Equation 1 by the comparison between the original X-ray image $X$ and the corresponding reconstructed X-ray image $X''$. That comparison further facilitates training the AI based model 320 to produce meaningful constituent images in decomposing input X-ray images. In particular, that comparison verifies that the decomposed set of constituent images are non-arbitrary in as much as they recombine to substantially form a facsimile of the original X-ray image.

In an embodiment, the loss function can be implemented using one or more loss functions other than the loss function defined by Equation 1. In an embodiment, the loss function can be implemented using a combination of loss functions. In an embodiment, the combination of loss functions includes the loss function defined by Equation 1. In an embodiment, the combination of loss functions excludes the loss function defined by Equation 1.

In an embodiment, training component 408 computes error associated with an original X-ray image and a reconstructed X-ray image using the data fidelity term. In an embodiment, training component 408 generates a confidence score based on the error computed using the data fidelity term. In an embodiment, the confidence score is a metric that quantifies a quality of a decomposition process. In an embodiment, the confidence score is indicative of an accuracy associated with one or more enhanced image representations generated using constituent images obtained through the decomposition process.

The loss function of Equation 1 further includes a regularization term that operates on each constituent image to reduce variance of the AI based model 320 without substantially increasing a bias of the AI based model 320. In an embodiment, the regularization term operates to mitigate style loss, adversarial loss, or a combination thereof.

In an embodiment, training component 408 can train a post-processing AI model to perform an image processing/analysis task on enhanced image representations to improve sensitivity of diagnostic decision making (e.g., early detection of lung diseases in X-ray images). Examples of image processing/analysis tasks include: organ segmentation, anomaly detection, anatomical feature characterization, medical image reconstruction, diagnosis, and the like. In an embodiment, the post-processing AI model performs image processing/analysis task based on an enhanced image representation, an associated original X-ray image, or a combination thereof.

In an embodiment, training component 408 receives the training data 450 directly from one or more medical imaging devices (e.g., a computed tomography (CT) scanner). In an embodiment, training component 408 receives the training data 450 from a remote computing device via a network interface. In an embodiment, training component 408 receives the training data 450 from a database or data structure that is accessible to X-ray decomposition component 402. In an embodiment, the database or data structure resides in memory 404. In an embodiment, the database or data structure is accessible to X-ray decomposition component 402 via a network interface.

Rendering component 410 can generate displays for presentation to a user of system 400. In an embodiment, rendering component generates a display that includes an original X-ray image (e.g., original X-ray image 350) and an enhanced image representation (e.g., enhanced image representation 355) generated using the original X-ray image.

Selection component 412 provides for selecting particular features of interest to selectively mask or generate. In an embodiment, selection component 412 generates a user interface element configured to receive user input for selecting the particular features of interest to selectively mask or generate. In an embodiment, a selection corresponding to the particular features of interest to selectively mask or generate modifies operation of AI component 312. For example, a selection corresponding to the particular features of interest to selectively mask or generate may define the subset of the features of interest discussed above with respect to AI component 312. As another example, a selection corresponding to the particular features of interest to selectively mask or generate may define the remaining features of interest in the set that are external to the subset discussed above with respect to AI component 312. In an embodiment, selection component 412 forwards user interface elements to rendering component 410 for inclusion on a display presented to a user of system 400. subset of the features of interest and suppresses remaining features of interest in the set that are external to the subset Each of the systems shown in FIGS. 3-4 may be implemented via any type of computing device, such as computer 1102 described in greater detail below with respect to FIG. 11. Each system shown in FIGS. 3-4 may comprise a single device or multiple devices cooperating in a distributed environment. For instance, X-ray decomposition components 302 and/or 402 may be provided via multiple devices arranged in a distributed environment that collectively provide the functionality described herein. Additionally, other components not shown may also be included within the distributed environment.

Figure 5:
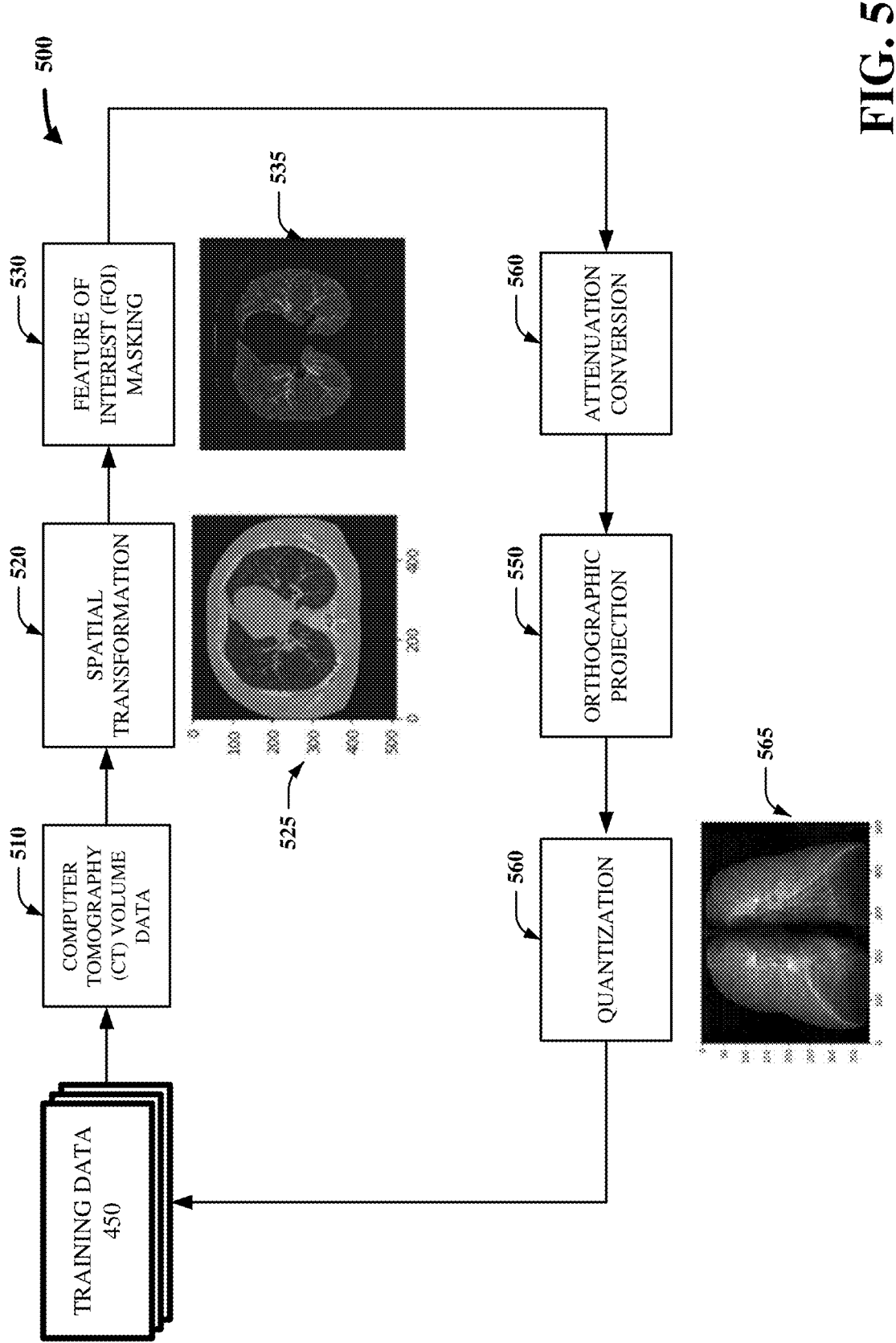
FIG. 5 illustrates an example process for generating ground truth constituent images from computed tomography (CT) volume data, in accordance with one or more embodiments described herein.

FIG. 5 illustrates an example process 500 for generating GT constituent images that highlights a given feature of interest from CT volume data, in accordance with one or more embodiments described herein. In FIG. 5, the given feature of interest is lung tissue. However, one skilled in the art will recognize that constituent images may highlight other features of interest or combinations of features of interest in accordance with embodiments of the present disclosure. For example, a constituent image may highlight heart tissue, or all anatomy of a patient located in an anterior section of the patient relative to a coronal plane.

At block 510, training component 408 retrieves CT volume data from training data 450 that corresponds to image data reconstructed from a particular CT scan operation. The retrieved CT volume data includes a plurality of voxels that are each assigned a radiodensity value. The radiodensity value quantifies a density of a medium (e.g., tissue) measured at a given location by the CT scan generating the retrieved CT volume data. Each radiodensity value is expressed as a dimensionless unit (i.e., a Hounsfield Unit (HU)) on a scale that linearly transforms a corresponding attenuation coefficient value to the scale where water and air are assigned HU values of 0 HU and −1000 HU, respectively. In an embodiment, the retrieved CT volume data comprises a respective HU value that falls within a range defined by −1024 HU and 1024 HU.

Each HU value represents a grayscale value assigned to a given voxel in the CT volume data. Air is generally associated with a lower value (e.g., −1024 HU) on the Hounsfield scale, and accordingly appears white in CT image data. Bone tissue is generally associated with a higher value (e.g., 1024 HU) on the Hounsfield scale, and accordingly appears black in CT image data. Other media (e.g, muscle tissue and fat tissue) are associated with intermediate values (e.g., 50 HU and −100 HU, respectively) on the Hounsfield scale, and accordingly appear in various shades of gray in CT image data.

At block 520, training component 408 spatially transforms the CT volume data in accordance with a view requirement defined for the given feature of interest. Spatially transforming the CT volume data involves aligning slices of the CT volume data with an intended orientation of the given feature of interest within the enhanced image representation. By way of example, image 525 represents a slice of CT volume data depicting the lung tissue feature of interest following spatial transformation of the CT volume data.

In an embodiment, a constituent image definition of the given feature of interest provides the view requirement that training component 408 utilizes for the spatial transformation. In an embodiment, training component 408 utilizes gantry angle data or projection angle data associated with the CT volume data for the spatial transformation. In an embodiment, training component 408 spatially transforms the CT volume data by applying a transformation matrix that modifies coordinate values associated with the CT volume data. In this embodiment, application of the transformation matrix rotates the CT volume data in accordance with the intended orientation of the given feature of interest within the GT constituent image.

At block 530, training component 408 performs a masking process on the CT volume data based on a range of HU values defined for the given feature of interest. In an embodiment, a constituent image definition of the given feature of interest provides the range of HU values that training component 408 utilizes for the masking process. The masking process that training component 408 performs involves evaluating a HU value of each voxel of the CT volume data. Based on that evaluation, training component 408 retains HU values that fall within the defined range of HU values and removes or minimizes HU values that fall outside of the defined range of HU values.

In doing so, training component 408 retains voxels of the CT volume data that correspond to the given feature of interest while removing or minimizing voxels that correspond to other features of interest. In an embodiment, training component 408 minimizes each HU value that falls outside of the defined range of HU values by replacing that HU value with a lower HU value on the Hounsfield scale (e.g., −1000 HU—the HU value assigned to air). Continuing with the example above, image 535 represents the slice of CT volume data depicted in image 525 following the masking process in which voxels corresponding to the lung tissue feature of interest were retained while voxels corresponding to the other features of interest were minimized.

At block 540, training component 408 converts HU values of the CT volume data into corresponding linear attenuation coefficient values. In an embodiment, training component 408 utilizes CT scan parameters associated with the CT volume data in converting the HU values into corresponding linear attenuation coefficient values. At block 550, training component 408 applies a projection matrix to the CT volume data. The projection matrix applied by training component 408 maps each voxel from a three-dimensional space of the CT volume data into a two-dimensional image plane to generate a two-dimensional intensity image. In an embodiment, the projection matrix is an orthogonal projection matrix.

At block 560, training quantization component 408 performs a quantization process on the two-dimensional intensity image to generate the GT constituent image depicting the given region of interest. The quantization process that training component 408 performs involves converting a continuous range of grayscale values represented in the two-dimensional intensity image to a set of discrete grayscale values. Continuing with the example above, image 565 represents a GT constituent image corresponding to the slice of CT volume data depicted in image 535 following the attenuation coefficient conversion of block 540, the application of the projection matrix in block 550, and the masking process of block 560. In an embodiment, the set of discrete grayscale values corresponds to a dynamic range of the GT constituent image. In an embodiment, training component 408 stores the GT constituent image in training data 450 subsequent to performing the quantization process.

Figure 6:
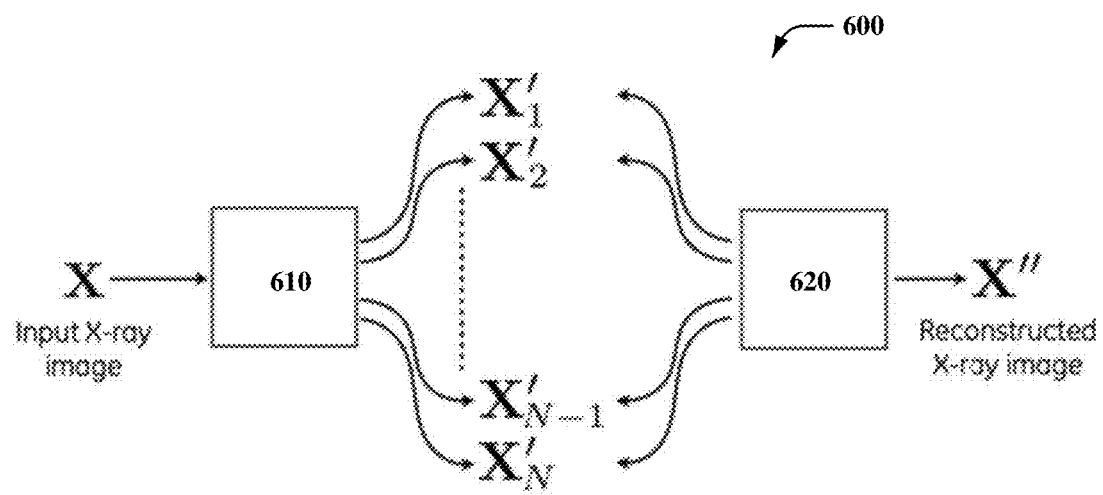
FIG. 6 illustrates an example network architecture for an artificial-intelligence-based model that facilitates generating enhanced image representations from original X-ray images, in accordance with one or more embodiments described herein.

FIG. 6 illustrates an example network architecture 600 for an AI based model that facilitates generating enhanced image representations from original X-ray images, in accordance with one or more embodiments described herein. As illustrated by FIG. 6, the example network architecture 600 includes a first AI subsystem 610 and a AI subsystem 620. The first AI subsystem 610 decomposes an input (or original) X-ray image X into a set of constituent images (i.e., constituent image $X'_1$ to constituent image $X'_N$). In an embodiment, each constituent image in the set of constituent images is associated with a different constituent image definition that training component 408 utilizes in training the first AI subsystem 610.

Each constituent image in the set of constituent images corresponds to a different feature of interest included in the input X-ray image X. Stated differently, each constituent image highlights, accentuates, or enhances a specific feature of interest included in the input X-ray image X. As such, each constituent image in a set of constituent images output by the first AI subsystem 610 corresponds to image data that AI component 312 of FIGS. 3-4 utilizes to generate one or more enhanced image representations.

The second AI subsystem 620 reconstructs the input X-ray image X by combining, at least, a subset of the set of constituent images to generate a reconstructed X-ray image X". As discussed above, a comparison between an input (or original) X-ray images and a corresponding reconstructed X-ray image generated using constituent images associated with the input X-ray image facilitates self-regularization of the AI based model. For example, that comparison between the input X-ray image and the corresponding reconstructed X-ray image provides input to the data fidelity term of the loss function discussed above with respect to training component 408 of FIG. 4.

Figure 7:
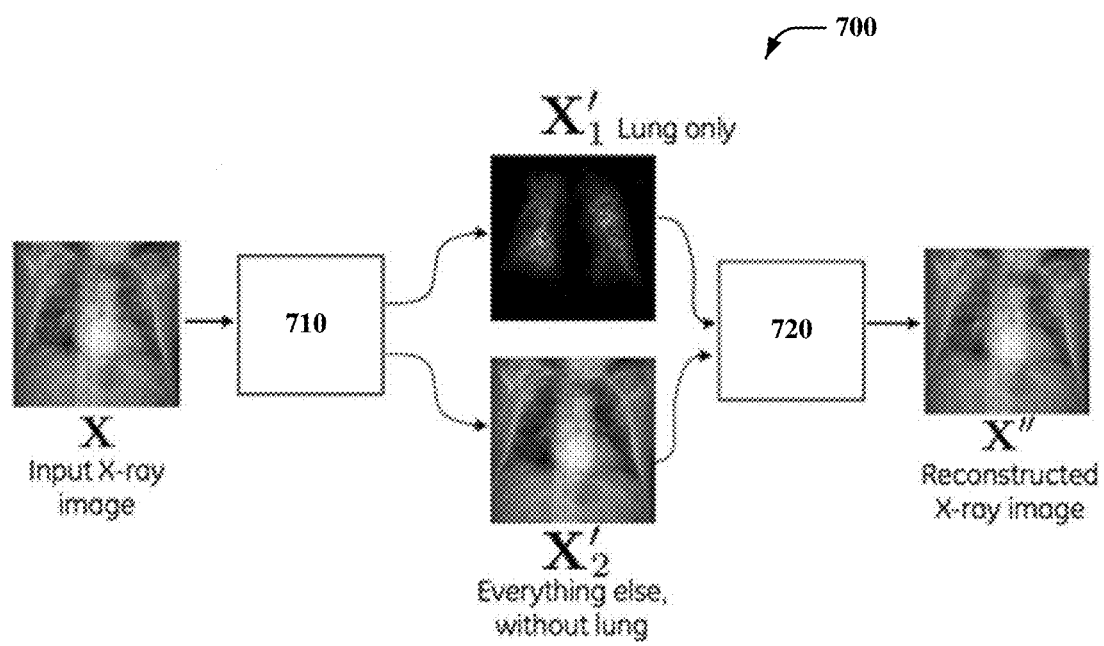
FIG. 7 illustrates another example network architecture for an artificial-intelligence-based model that facilitates generating enhanced image representations from original X-ray images, in accordance with one or more embodiments described herein.

FIG. 7 illustrates another example network architecture 700 for an AI based model that facilitates generating enhanced image representations from original X-ray images, in accordance with one or more embodiments described herein. As illustrated in FIG. 7, the example network architecture 700 includes a first AI subsystem 710 and a second AI subsystem 720. Similar to the first AI subsystem 610 of FIG. 6, the first AI subsystem 710 of FIG. 7 decomposes an input (or original) X-ray image X into a set of constituent images. Likewise, the second AI subsystem 720 reconstructs the input X-ray image X by combining, at least, a subset of the set of constituent images to generate a reconstructed X-ray image X".

A comparison between FIG. 6 and FIG. 7 shows that the first AI subsystem 710 decomposes an input X-ray image into fewer constituent images than the first AI subsystem 610. This difference illustrates one aspect of constituent image definitions within embodiments of the present disclosure. In an embodiment, a correspondence exists between a number of constituent image definitions that training component 408 utilizes in training an AI subsystem for decomposing original X-ray images and a number of constituent images output by that convolutional neural network.

In training the first AI subsystem 610 of FIG. 6, training component 408 utilized, at least, four constituent image definitions. As a result, the first AI subsystem 610 decomposes an input X-ray image into, at least, four constituent images (i.e., constituent images $X'_1$ to $X'_N$). In training the first AI subsystem 710 of FIG. 7, training component 408 utilized two constituent image definitions. Those two constituent image definitions include: a first constituent image definition associated with lung tissue; and a second constituent image definition associated with each remaining feature of interest external to lung tissue (e.g., bone tissue) that is included in an original X-ray image. As a result, the first AI subsystem 710 decomposes an input X-ray image into two constituent images (i.e., constituent images $X'_1$ and $X'_2$).

Figure 8:
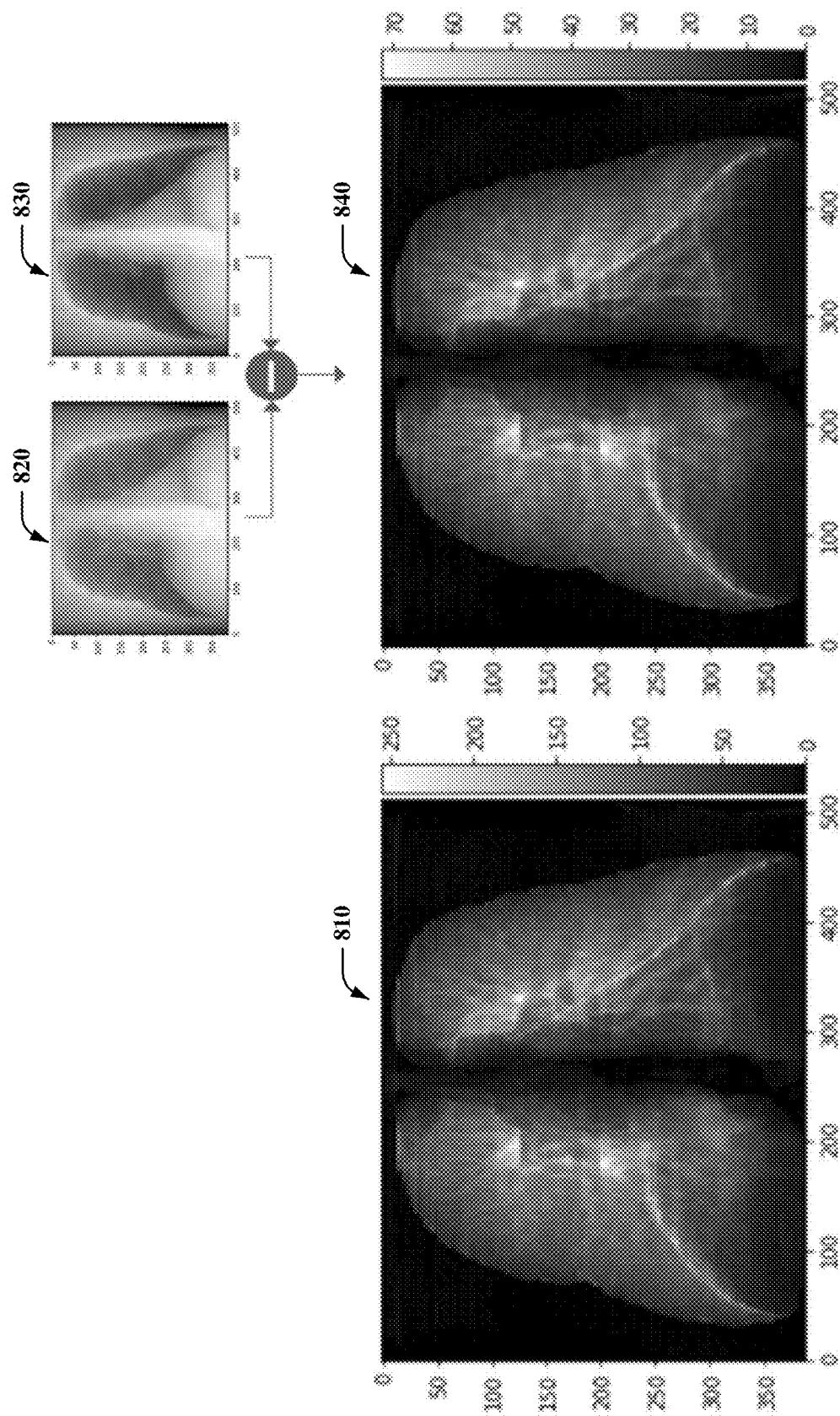
FIG. 8 illustrates example image data comparing an enhanced image representation generated from CT volume data with an enhanced image representation generated from an original X-ray image, in accordance with one or more embodiments described herein.

FIG. 8 illustrates example image data comparing an enhanced image representation 810 generated from CT volume data with an enhanced image representation 840 generated from an original X-ray image, in accordance with one or more embodiments described herein. In FIG. 8, lung tissue is the feature of interest that enhanced image representations 810 and 840 each highlight. Enhanced image representation 810 was generated using the example process 500 discussed above with respect to FIG. 5. Enhanced image representation 830 was generated using a constituent image obtained by providing original X-ray image 820 as an input to AI based model 320. FIG. 8 depicts enhanced image representation 830 as highlighting each remaining feature of interest external to lung tissue. Enhanced image representation 840 is a difference image formed by subtracting enhanced image representation 830 from original X-ray image 820. As seen in FIG. 8, enhanced image representations 810 and 840 exhibit comparable spatial resolution. In some embodiments, enhanced image representations derived from original X-ray images (e.g., enhanced image representation 840) may exhibit a reduction in dynamic range relative to enhanced X-ray images derived from CT volume data.

Figure 9:
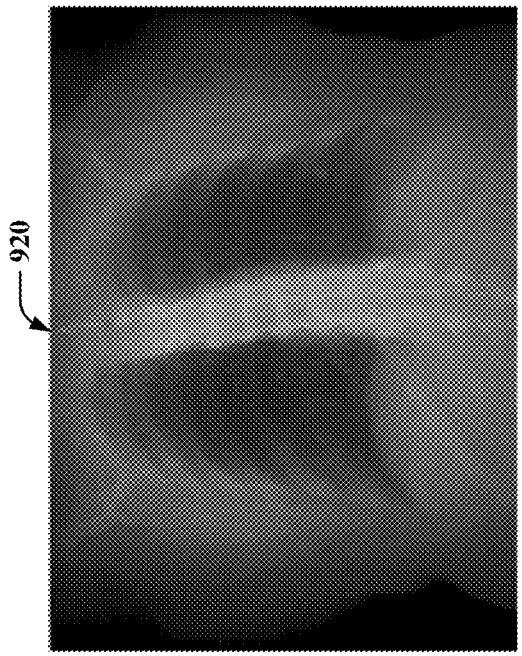
FIG. 9 illustrates enhanced image representations corresponding to spatial location definitions, in accordance with one or more embodiments described herein.
Figure 9:
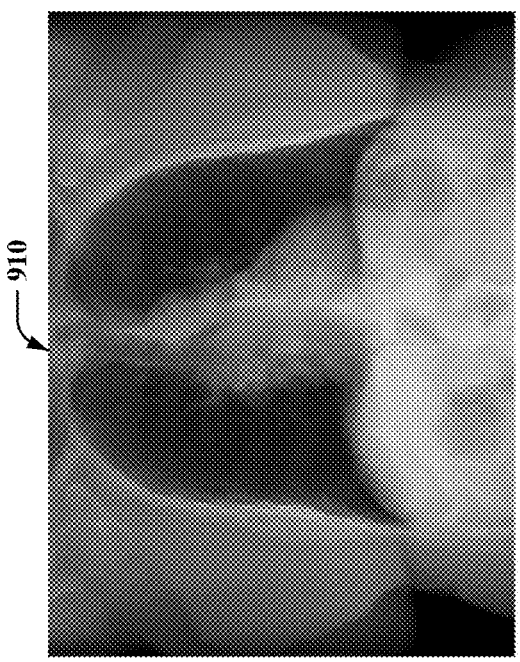

FIG. 9 illustrates another aspect of constituent definitions within embodiments of the present disclosure. In particular, each constituent definition that training component 408 utilizes in training AI based models to decompose original X-ray images can be application specific. Each constituent image or enhanced image representation discussed above that AI component 312 generates based on such constituent images correspond to a tissue type definition. For example, FIG. 2 illustrates enhanced image representations that highlight lung tissue, bone tissue, and epithelial tissue (i.e., enhanced image representations 220, 230, and 240, respectively).

As illustrated by FIG. 9, training component 408 can utilize other types of constituent definitions in training AI based models to decompose original X-ray images. By way of example, training component 408 utilized spatial location definitions in training an AI based model to decompose an original X-ray image into the constituent images associated with enhanced image representations 910 and 920. In this example, AI component 312 utilized such constituent images to generate enhanced image representation 910 that highlights features of interest associated with an anterior region of an original X-ray image and enhanced image representation 920 that highlights features of interest associated with a posterior region of the original X-ray image. Other spatial location definitions may distinguish between left and right regions of an original X-ray image; superior and inferior regions of an original X-ray image; and the like.

As another example, training component 408 may utilize constituent definitions that distinguish between natural and foreign features of interest within an original X-ray image in training artificial-intelligence-based models to decompose original X-ray images. In this example, a first constituent definition may correspond to an implant or a peripherally inserted central catheter (PICC) line while a second constituent definition may correspond to epithelial tissue.

As another example, training component 408 may utilize constituent definitions that distinguish between latent properties of a feature of interest within an original X-ray image. Such constituent definitions may facilitate material decomposition processing. In this example, a first constituent definition may correspond to a first basis material of a multi-material object and a second constituent definition may correspond to a second basis material of the multi-material object.

Figure 10:
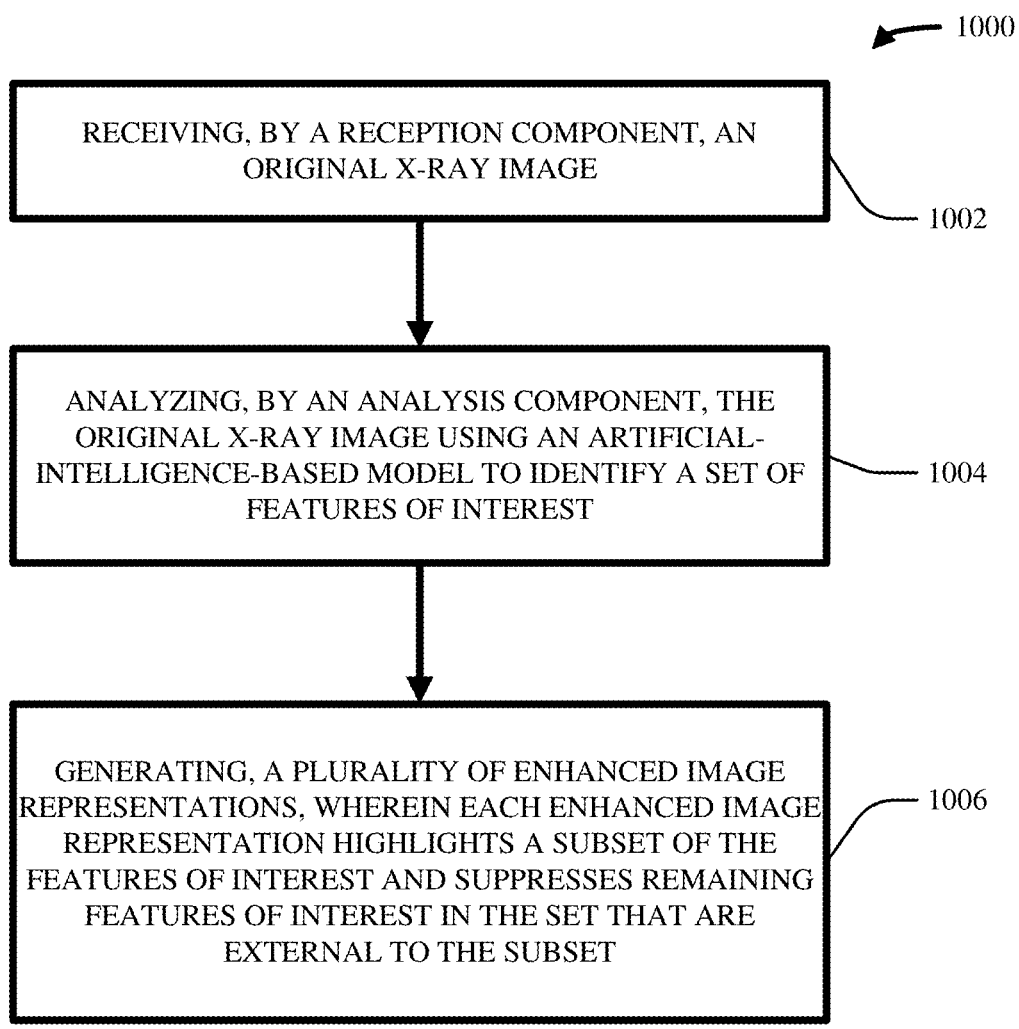
FIG. 10 is a flow-chart illustrating an example of a method of generating enhanced image representations, in accordance with one or more embodiments described herein.

FIG. 10 is a flow-chart illustrating an example of a method of generating enhanced image representations, in accordance with one or more embodiments described herein. At block 1002, method 1000 includes receiving, by a reception component (e.g., reception component 308 of FIGS. 3-4), an original X-ray image. At block 1004, method 1000 includes analyzing, by an analysis component (e.g., analysis component 310 of FIGS. 3-4), the original X-ray image using an AI based model to identify a set of features of interest. At block 1006, method 1000 includes generating, by an AI component (e.g., AI component 312 of FIGS. 3-4), a plurality of enhanced image representations. Each enhanced image representation highlights a subset of the features of interest and suppresses remaining features of interest in the set that are external to the subset.

In an embodiment, method 1000 further includes training, by a training component, the AI based model using machine learning. In an embodiment, method 1000 further includes utilizing, by the training component, information as training data that is derived from other imaging modalities or different forms of a same imaging modality, including: computed tomography (CT) volumes, magnetic resonance imaging (MRI) data, positron emission tomography (PET) data, multi-energy X-ray imaging data, or a combination thereof. In an embodiment, method 1000 further includes improving sensitivity of diagnostic decision making, by the training component, by employing a set of original X-ray images and a set of corresponding enhanced image representations to generate at least one of diagnosis or segmentation. In an embodiment, method 1000 further includes computing, by the training component, error associated with the original X-ray image and the reconstructed X-ray image. In an embodiment, method 1000 further includes generating, by the training component, a confidence score associated with the plurality of enhanced image representations.

In an embodiment, method 1000 further includes displaying, by a rendering component, the original X-ray image and the enhanced X-ray image. In an embodiment, method 1000 further includes generating, by the rendering component, a display that compares difference between the original X-ray image and the enhanced image representation. In an embodiment, method 1000 further includes providing, by a selection component, particular features of interest to selectively mask or generate.

In an embodiment, method 1000 further includes using a first AI subsystem to decomposes the original X-ray image into a set of constituent images and using a second AI subsystem to combine a subset of the constituent images to generate a reconstructed X-ray image. In an embodiment, an error value is generated based on a comparison of the original X-ray image to the reconstructed X-ray image.

Figure 11:
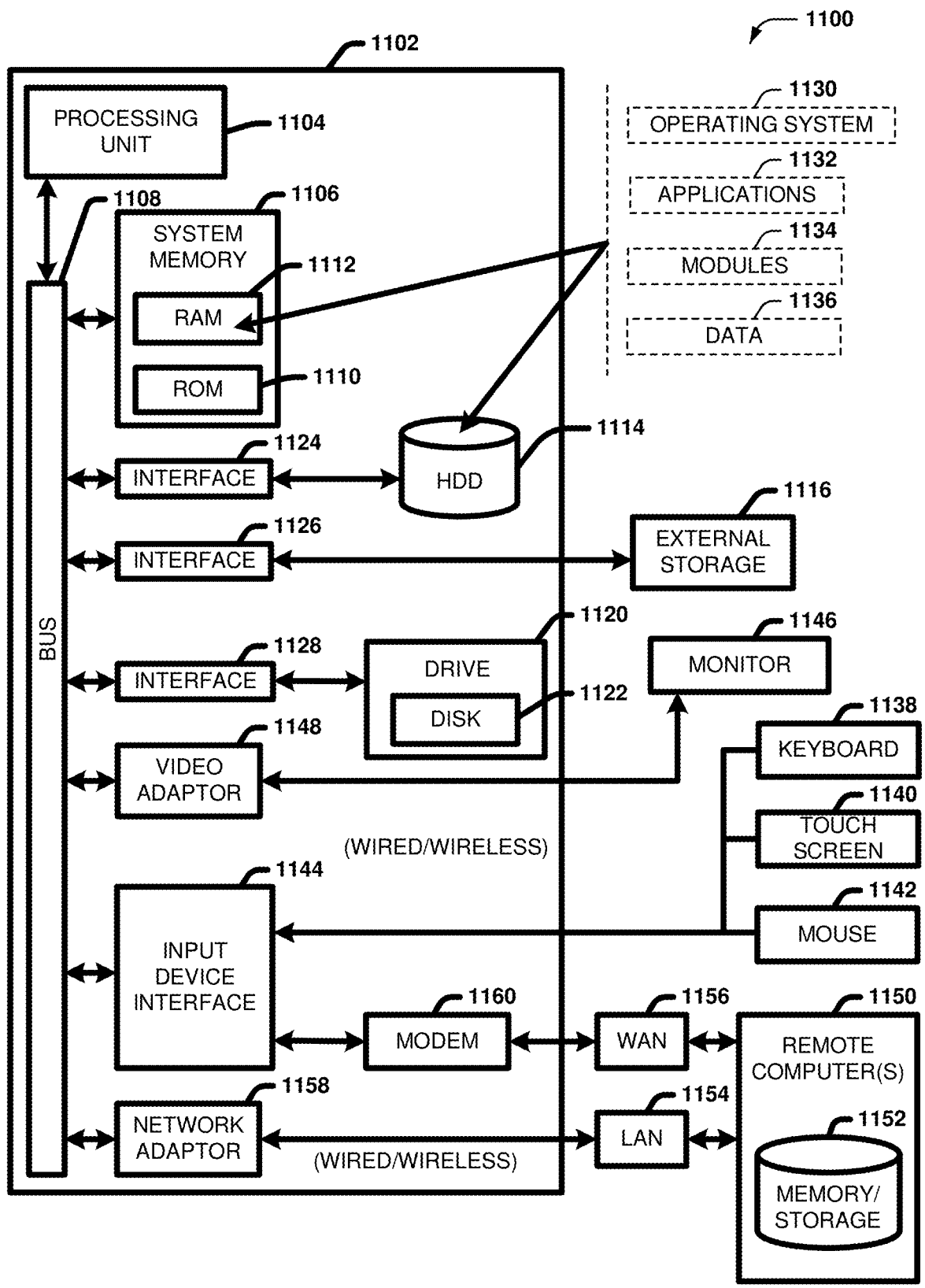
FIG. 11 illustrates a block diagram of an example, non-limiting operating environment in which one or more embodiments described herein can be facilitated.

FIG. 11 can provide a non-limiting context for the various aspects of the disclosed subject matter, intended to provide a general description of a suitable environment in which the various aspects of the disclosed subject matter can be implemented. FIG. 11 illustrates a block diagram of an example, non-limiting operating environment in which one or more embodiments described herein can be facilitated. Repetitive description of like elements employed in other embodiments described herein is omitted for sake of brevity.

With reference to FIG. 11, a suitable operating environment 1100 for implementing various aspects of this disclosure can also include a computer 1102. The computer 1102 can also include a processing unit 1104, a system memory 1106, and a system bus 1108. The system bus 1108 couples system components including, but not limited to, the system memory 1106 to the processing unit 1104. The processing unit 1104 can be any of various available processors. Dual microprocessors and other multiprocessor architectures also can be employed as the processing unit 1104. The system bus 1108 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MCA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 11124), and Small Computer Systems Interface (SCSI).

The system memory 1106 can also include volatile memory 1110 and nonvolatile memory 1112. The basic input/output system (BIOS), containing the basic routines to transfer information between elements within the computer 1102, such as during start-up, is stored in nonvolatile memory 1112. Computer 1102 can also include removable/non-removable, volatile/non-volatile computer storage media. FIG. 11 illustrates, for example, a disk storage 1114. Disk storage 1114 can also include, but is not limited to, devices like a magnetic disk drive, floppy disk drive, tape drive, Jaz drive, Zip drive, LS-100 drive, flash memory card, or memory stick. The disk storage 1114 also can include storage media separately or in combination with other storage media. To facilitate connection of the disk storage 1114 to the system bus 1108, a removable or non-removable interface is typically used, such as interface 1116. FIG. 11 also depicts software that acts as an intermediary between users and the basic computer resources described in the suitable operating environment 1100. Such software can also include, for example, an operating system 1118. Operating system 1118, which can be stored on disk storage 1114, acts to control and allocate resources of the computer 1102.

System applications 1120 take advantage of the management of resources by operating system 1118 through program modules 1122 and program data 1124, e.g., stored either in system memory 1106 or on disk storage 1114. It is to be appreciated that this disclosure can be implemented with various operating systems or combinations of operating systems. A user enters commands or information into the computer 1102 through input device(s) 1136. Input devices 1136 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1104 through the system bus 1108 via interface port(s) 1130. Interface port(s) 1130 include, for example, a serial port, a parallel port, a game port, and a universal serial bus (USB). Output device(s) 1134 use some of the same type of ports as input device(s) 1136. Thus, for example, a USB port can be used to provide input to computer 1102, and to output information from computer 1102 to an output device 1130. Output adapter 1128 is provided to illustrate that there are some output devices 1134 like monitors, speakers, and printers, among other output devices 1134, which require special adapters. The output adapters 1128 include, by way of illustration and not limitation, video and sound cards that provide a means of connection between the output device 1134 and the system bus 1108. It should be noted that other devices and/or systems of devices provide both input and output capabilities such as remote computer(s) 1140.

Computer 1102 can operate in a networked environment using logical connections to one or more remote computers, such as remote computer(s) 114. The remote computer(s) 1140 can be a computer, a server, a router, a network PC, a workstation, a microprocessor based appliance, a peer device or other common network node and the like, and typically can also include many or all of the elements described relative to computer 1102. For purposes of brevity, only a memory storage device 1142 is illustrated with remote computer(s) 1140. Remote computer(s) 1140 is logically connected to computer 1102 through a network interface 1138 and then physically connected via communication connection 1132. Network interface 1138 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 1132 refers to the hardware/software employed to connect the network interface 1138 to the system bus 1108. While communication connection 1132 is shown for illustrative clarity inside computer 1102, it can also be external to computer 1102. The hardware/software for connection to the network interface 1138 can also include, for exemplary purposes only, internal and external technologies such as, modems including regular telephone grade modems, cable modems and DSL modems, ISDN adapters, and Ethernet cards.

One or more embodiments described herein can be a system, a method, an apparatus and/or a computer program product at any possible technical detail level of integration. The computer program product can include a computer readable storage medium (or media) having computer readable program instructions thereon for causing a processor to carry out aspects of one or more embodiment. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. In this regard, in various embodiments, a computer readable storage medium as used herein can include non-transitory and tangible computer readable storage mediums.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of one or more embodiments can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of one or more embodiments.

Aspects of one or more embodiments are described herein with reference to flowchart illustrations and/or block diagrams of methods, apparatus (systems), and computer program products according to embodiments. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and other devices to function in a particular manner, such that the computer readable storage medium having instructions stored therein comprises an article of manufacture including instructions which implement aspects of the function/act specified in the flowchart and block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and block diagram block or blocks.

The flowchart and block diagrams in the Figures illustrate the architecture, functionality, and operation of possible implementations of systems, methods, and computer program products according to various embodiments described herein. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and flowchart illustration, and combinations of blocks in the block diagrams and flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on one or more computers, those skilled in the art will recognize that this disclosure also can or can be implemented in combination with other program modules. Generally, program modules include routines, programs, components, data structures, etc. that perform particular tasks or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices. For example, in one or more embodiments, computer executable components can be executed from memory that can include or be comprised of one or more distributed memory units. As used herein, the term "memory" and "memory unit" are interchangeable. Further, one or more embodiments described herein can execute code of the computer executable components in a distributed manner, e.g., multiple processors combining or working cooperatively to execute code from one or more distributed memory units. As used herein, the term "memory" can encompass a single memory or memory unit at one location or multiple memories or memory units at one or more locations.

As used in this application, the terms "component," "system," "platform," "interface," and the like, can refer to and can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and a computer. By way of illustration, both an application running on a server and the server can be a component. One or more components can reside within a process or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that can provide specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

The term "facilitate" as used herein is in the context of a system, device or component "facilitating" one or more actions or operations, in respect of the nature of complex computing environments in which multiple components and/or multiple devices can be involved in some computing operations. Non-limiting examples of actions that may or may not involve multiple components and/or multiple devices comprise transmitting or receiving data, establishing a connection between devices, determining intermediate results toward obtaining a result (e.g., including employing ML and/or AI techniques to determine the intermediate results), etc. In this regard, a computing device or component can facilitate an operation by playing any part in accomplishing the operation. When operations of a component are described herein, it is thus to be understood that where the operations are described as facilitated by the component, the operations can be optionally completed with the cooperation of one or more other computing devices or components, such as, but not limited to: sensors, antennae, audio and/or visual output devices, other devices, etc.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches, and gates, in order to optimize space usage or enhance performance of user equipment. A processor can also be implemented as a combination of computing processing units. In this disclosure, terms such as "store," "storage," "data store," "data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a memory that stores computer executable components; and
a processor that executes the computer executable components stored in the memory, wherein the computer executable components comprise:
a reception component that receives an original X-ray image;
an analysis component that analyzes the original X-ray image using an artificial intelligence (AI) based model with respect to a set of features of interest and generates a set of constituent images of the original X-ray image corresponding to the set of features of interest; and
an AI component that generates a plurality of enhanced image representations by partitioning the set of constituent images into a first subset associated with features of interest to be highlighted and a second subset associated with features of interest to be suppressed for respective enhanced images and applying image processing functions to the first and second subsets of constituent images to respectively highlight and suppress the features of interest in the respective enhanced image.

2. The system of claim 1, further comprising a training component that employs machine learning to train the AI based model.

3. The system of claim 2, wherein the training component utilizes information as training data that is derived from other imaging modalities or different forms of a same imaging modality, including: computed tomography (CT) volumes, magnetic resonance imaging (MRI) data, positron emission tomography (PET) data, multi-energy X-ray imaging data, or a combination thereof.

4. The system of claim 1, further comprising a rendering component that displays the original X-ray image and an enhanced image representation from the plurality of enhanced image representations.

5. The system of claim 2, wherein the training component employs a set of original X-ray images and a set of corresponding enhanced image representations to generate at least one of diagnosis or segmentation to improve sensitivity of diagnostic decision making.

6. The system of claim 5, wherein the at least one of diagnosis or segmentation to improve sensitivity of diagnostic decision making includes early detection of lung diseases in X-ray images.

7. The system of claim 1, further comprising a selection component that provides for selecting particular features of interest to selectively mask or generate.

8. The system of claim 1, wherein the AI based model comprises a first AI subsystem that decomposes the original X-ray image into the set of constituent images and a second AI subsystem that combines a subset of the constituent images to generate a reconstructed X-ray image of the original X-ray image, wherein an error value is generated based on a comparison of the original X-ray image to the reconstructed X-ray image.

9. The system of claim 8, wherein a confidence score associated with the plurality of enhanced image representations is generated based on the error value.

10. The system of claim 2, wherein the training component utilizes a loss function.

11. A method, comprising:
receiving, by a reception component, an original X-ray image;
analyzing, by an analysis component, the original X-ray image using an artificial intelligence (AI) based model to identify a set of features of interest;
generating, by the analysis component, a set of constituent images of the original X-ray image corresponding to the set of features of interest;
partitioning, by an AI component, the set of constituent images into a first subset associated with features of interest to be highlighted and a second subset associated with features of interest to be suppressed for respective enhanced images;
applying, by the AI component, image processing functions to the first and second subsets of constituent images to respectively highlight and suppress the features of interest in the respective enhanced image; and generating, by the AI component, a plurality of enhanced image representations from the first and second subsets of constituent images.

12. The method of claim 11, further comprising training, by a training component, the AI based model using machine learning.

13. The method of claim 12, further comprising utilizing, by the training component, information as training data that is derived from other imaging modalities or different forms of a same imaging modality, including: computed tomography (CT) volumes, magnetic resonance imaging (MRI) data, positron emission tomography (PET) data, multi-energy X-ray imaging data, or a combination thereof.

14. The method of claim 12, further comprising improving sensitivity of diagnostic decision making, by the training component, by employing a set of original X-ray images and a set of corresponding enhanced image representations to generate at least one of diagnosis or segmentation.

15. The method of claim 11, further comprising generating, by a rendering component, a display that compares a difference between the original X-ray image and an enhanced image representation from the plurality of enhanced image representations.

16. The method of claim 11, further comprising providing, by a selection component, particular features of interest to selectively mask or generate.

17. The method of claim 11, further comprising:
using a first AI subsystem to decompose the original X-ray image into the set of constituent images; and
using a second AI subsystem to combine a subset of the constituent images to generate a reconstructed X-ray image,
wherein an error value is generated based on a comparison of the original X-ray image to the reconstructed X-ray image.

18. The method of claim 17, further comprising:
generating a confidence score associated with the plurality of enhanced image representations using the error value.

19. The method of claim 12, further comprising utilizing, by the training component, a loss function.

20. A computer program product for facilitating generating of enhanced image representations, the computer program product comprising a non-transitory computer readable medium having program instructions embodied therewith, the program instructions executable by a processing component to cause the processing component to:
receive an original X-ray image;
analyze the original X-ray image using an artificial-intelligence-based model to identify a set of features of interest;
generate a set of constituent images of the original X-ray image corresponding to the set of features of interest;
partition the set of constituent images into a first subset associated with features of interest to be highlighted and a second subset associated with features of interest to be suppressed for respective enhanced images;
apply image processing functions to the first and second subsets of constituent images to respectively highlight and suppress the features of interest in the respective enhanced image; and
generate a plurality of enhanced image representations from the first and second subsets of constituent images.

* * * * *